US007441468B2

(12) United States Patent  (10) Patent No.: US 7,441,468 B2
Cox  (45) Date of Patent: Oct. 28, 2008

(54) SQUEEZE FORCE MEASURING SYSTEM

(75) Inventor: Charles H. Cox, Concord, VA (US)

(73) Assignee: C.B. Fleet Company, Incorporated, Lynchburg, VA (US)

( * ) Notice: Subject to any disclaimer, the term of this patent is extended or adjusted under 35 U.S.C. 154(b) by 161 days.

(21) Appl. No.: 11/283,606

(22) Filed: Nov. 17, 2005

(65) Prior Publication Data

US 2007/0119260 A1    May 31, 2007

(51) Int. Cl.
G01M 3/34    (2006.01)
G01N 3/08    (2006.01)

(52) U.S. Cl. .......................................... 73/820; 73/49.3

(58) Field of Classification Search ........... 73/818–825, 73/49.3, 41.3, 40–45.8, 862.454; 209/523
See application file for complete search history.

(56) References Cited

U.S. PATENT DOCUMENTS

| | | | | |
|---|---|---|---|---|
| 4,697,457 | A | * | 10/1987 | Fochtman et al. ............. 73/820 |
| 4,857,055 | A | * | 8/1989 | Wang ........................ 604/133 |
| 4,955,226 | A | * | 9/1990 | Beaty et al. .................. 73/49.3 |
| 5,226,316 | A | * | 7/1993 | Mally et al. .................. 73/49.3 |
| 5,767,392 | A | * | 6/1998 | Belcher et al. ................. 73/41 |
| 6,202,476 | B1 | * | 3/2001 | Fenlon ....................... 73/49.3 |
| 6,539,809 | B1 | * | 4/2003 | Weiss et al. ................... 73/825 |

FOREIGN PATENT DOCUMENTS

JP         2002122467 A  *  4/2002

OTHER PUBLICATIONS

American Medical Systems, "Acticon Neosphincter: Summary of Safety and Effectiveness Data" Jun. 12, 2002. <http://web.archive.org/web/20020612233007/http://www.fda.gov/cdrh/pdf/p010020.html>.*
Fenton et al. "Measurement of urine flow in catheterised patients using the gravimetric principle" Medical and Biological Engineering and Computing; vol. 22, No. 6, Nov. 1984. <http://www.springerlink.com/content/2u32110m02884378/fulltext.pdf>.*
Ametek TCI Division, "Chatillon® TCM201 Series Motorized Force Tester," located at http://www.chatillon.com/Our%20Products/Chatillon%20Force%20Testers/TCM201_forcetester.html, 1 page, 2005.
Ametek TCI Division, "Chatillon® TCD200 Series Digital Force Tester," located at http://www.chatillon.com/Our%20Products/Chatillon%20Force%20Testers/TCD200_forcetester.html, 1 page, 2005.

(Continued)

Primary Examiner—Edward Lefkowitz
Assistant Examiner—Jonathan Dunlap
(74) Attorney, Agent, or Firm—Evan Law Group LLC

(57) ABSTRACT

A method of measuring the squeeze force of a package includes applying a compression force to the package, and measuring the compression force as a function of volume change of the package. The compression force may be applied by placing the package in a force tester, and compressing the package with a movable crosshead. A device for measuring the squeeze force of a package containing a fluid may include a force tester and a fluid gauge, where the force tester includes a movable crosshead and a force gauge attached to the crosshead. The device may also include a holder to secure a bottle for testing.

27 Claims, 8 Drawing Sheets

OTHER PUBLICATIONS

Ametek TCI Division, "Chatillon® DFE Series Digital Force Gauge," located at http://www.chatillon.com/Our%20Products/Chatillon%20Force%20Gauge/DFE_forcegauge.html, 4 pages, 2005.

Imada, Inc., "MV-220 Motorized Vertical Test Stands," located at http://www.imada.com/mv-220.shtml, 2 pages, 2005.

Cal Poly Packaging Association, "Cal Poly Package Testing Equipment," located at http://www.calpoly.edu/~cppaclub/testequip.html, 3 pages, 2005.

The Society of the Plastics Industry, Inc., "Technical Bulletin-Vertical Compression Test," PBI 3-1968, Rev. 2-1990, 6 pages, 1990.

The Society of the Plastics Industry, Inc., "Technical Bulletin-Dead Load Compression Test," PBI 12-1978, Rev. 1-1990, 4 pages, 1990.

* cited by examiner

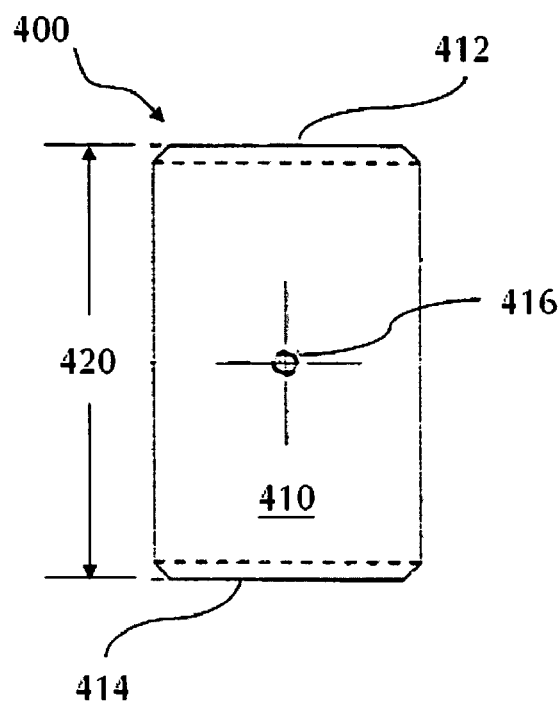
FIG. 4
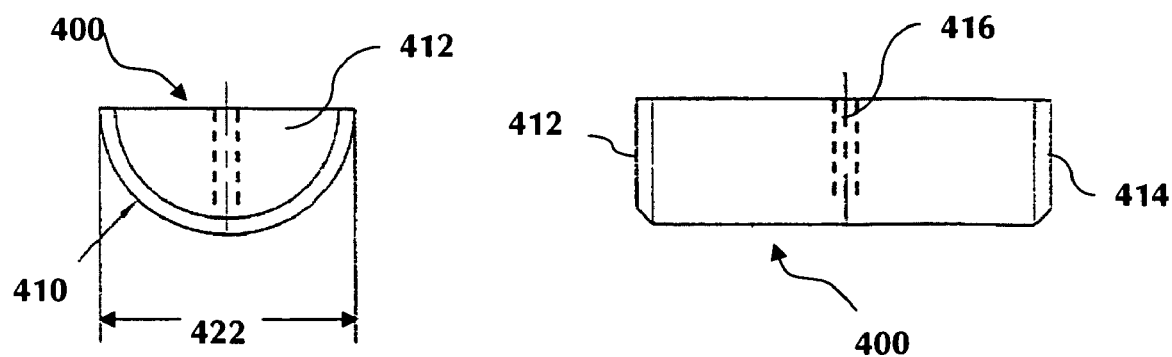
FIG. 5          FIG. 6

SQUEEZE FORCE MEASURING SYSTEM

BACKGROUND

Packages for a variety of products may be designed to provide for dispensing of the product by squeezing the package. Examples of products dispensed by squeezing include foods, such as condiments, salad dressings and yogurts; personal hygiene products, such as toothpastes, lotions, and hair care products; therapeutic products, such as eye drops, topical gels and creams, and liquid suppositories; and household products, such as caulks, silicone sealants, paints, and adhesives. A user may dispense these products intermittently or in a single use. The force required to squeeze the package affects the ease with which the product may be dispensed by a user.

One example of a product dispensed by squeezing is an enema. Enemas provide for the introduction of a fluid directly into the colon. Examples of enema fluids include water; hypertonic aqueous salt solutions; solutions or suspensions of cathartic agents, such as bisacodyl or phenolphthalein; and mineral oil. One area of development for enema products is a reduction in the squeeze force required to force the fluid contained in the enema bottle into the colon. Lower squeeze forces are particularly advantageous for elderly patients. Reliable measurement of the squeeze force for conventional and prototype enemas would facilitate this development.

It is desirable to provide a method of measuring the squeeze force required to dispense a product from a package. It is also desirable to provide a device for measuring this squeeze force. A system for accurately and reproducibly measuring squeeze force may provide valuable information for the testing and development of packaging designs and materials.

SUMMARY

In one aspect, the invention provides a method of measuring squeeze force including applying a compression force to a package and measuring the compression force as a function of volume change of the package.

In another aspect, the invention provides a method of measuring squeeze force of a package including placing the package in a force tester below a movable crosshead, compressing the package with the crosshead by a compression force, measuring the compression force applied to the package with a force gauge attached to the crosshead, measuring the volume change of the package, and correlating the measured compression force with the measured displaced volume change.

In yet another aspect, the invention provides a squeeze force measuring device including a force tester and a fluid gauge. The force tester includes a movable crosshead and a force gauge attached to the crosshead.

In yet another aspect, the invention provides a bottle holder for a force measuring device including a curved bottom wall extending linearly from a first end to a second end, a first end wall attached to the first end, and a second end wall attached to the second end.

In yet another aspect, the invention provides a squeeze force measuring device including means for applying a compression force to a package, and means for measuring the compression force as a function of volume change of the package.

The following definitions are included to provide a clear and consistent understanding of the specification and claims.

The term "package" means a container having an enclosed volume except for an opening in the container. Examples of packages include boxes, bottles and bags.

The term "squeeze force" means the compression force required to reduce the volume of a package by a particular amount.

The term "product" means a substance that may be contained in a package. The term includes substances used for measuring the squeeze force of the package. A product may be the same as or different from a substance intended for dispensing by a user.

The term "fluid" means a substance that may flow. Examples of fluids include liquids, gels, creams, pastes and thixotropic materials. Fluids may assume the shape of a package in which they are contained.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 4 is a top representation of a crosshead.

FIG. 5 is an end representation of a crosshead.

FIG. 6 is a side representation of a crosshead.

DETAILED DESCRIPTION

The present invention provides a method of measuring the squeeze force required to dispense a product from a package. The method includes applying a compression force to a package and measuring the compression force as a function of volume change of the package. The present invention also provides a squeeze force measuring device including a force tester, having a movable crosshead and a force gauge attached to the crosshead, and a fluid gauge. In addition, the present invention provides a holder that facilitates measuring the squeeze force of a bottle.

The method applies to a variety of package types and to a variety of products that may be present in a package. The method also may be adapted for use with a specific type of package, providing for comparison of squeeze forces of similar packages. The device for measuring squeeze force may provide accurate and consistent measurements for a variety of package types and packaged products. Squeeze force measurements may be advantageous in the design and testing of packages, particularly for packages adapted for consumer products.

Figure 1:
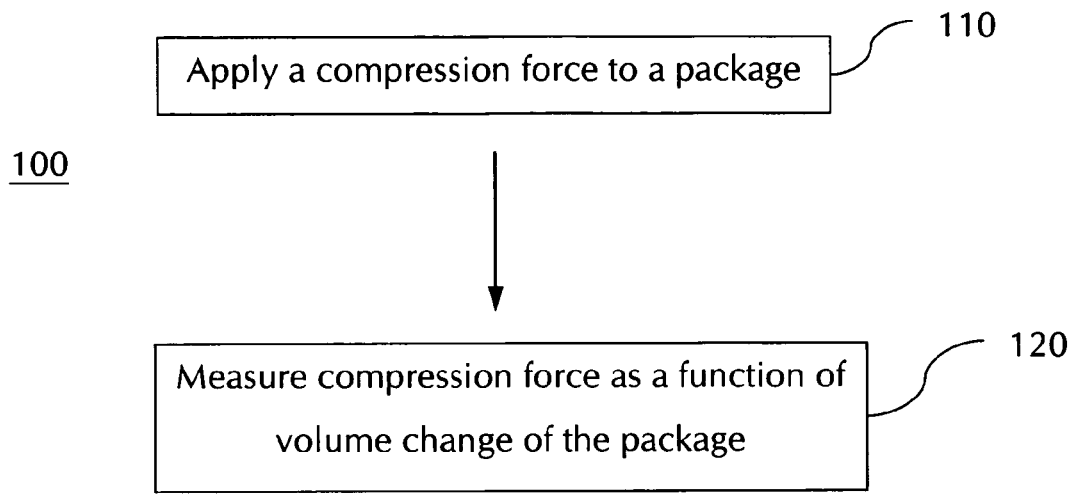
FIG. 1 represents a method of measuring squeeze force.

FIG. 1 represents a method 100 of measuring squeeze force for a package that includes applying a compression force to a package 110, and measuring the compression force as a function of volume change of the package 120. In 110 the compression force may be applied to the package manually or automatically.

In 120 the volume change may be determined by measuring the volume of the package once the compression force has been applied, and subtracting this volume from the volume of the package before the compression force was applied. In one example, the volume of a package can be measured by sealing the opening of the package and immersing the sealed package in a fluid. The increase in volume of the fluid is equal to the volume of the package, including the volume of the material of which the package is composed. In another example, the volume of a package may be measured by filling the package with a product and then removing the product and measuring the amount of the product. The use of a product to measure package volume may be advantageous in measuring the squeeze force of a package containing a product, since the volume change may be determined by measuring the amount of product displaced from the package. For a fluid product, the amount of fluid may be measured in different ways, including measuring the mass of the fluid and measuring the volume of the fluid, for example by displacing the fluid from the package to a fluid gauge.

Squeeze force may be expressed in one of two types of units, depending on whether the volume change is measured in absolute terms of volume or in relative terms of volume percentage. If the squeeze force is expressed as the compression force at a particular reduction in package volume, the units for squeeze force include pound-force@ x ounces (lb-f@ x oz.), Newtons@ x Liters (N@ x L), and dynes@ x milliliters (dynes@ x mL), where "x" is the total reduction in package volume at the measured compression force. If the squeeze force is expressed as the compression force at a particular percentage reduction in package volume, the units for squeeze force include lb-f@ y %, N@ y %, and dynes@ y %, where "y" is the reduction in package volume at the measured compression force as a percentage of the package volume prior to compression.

Figure 2:
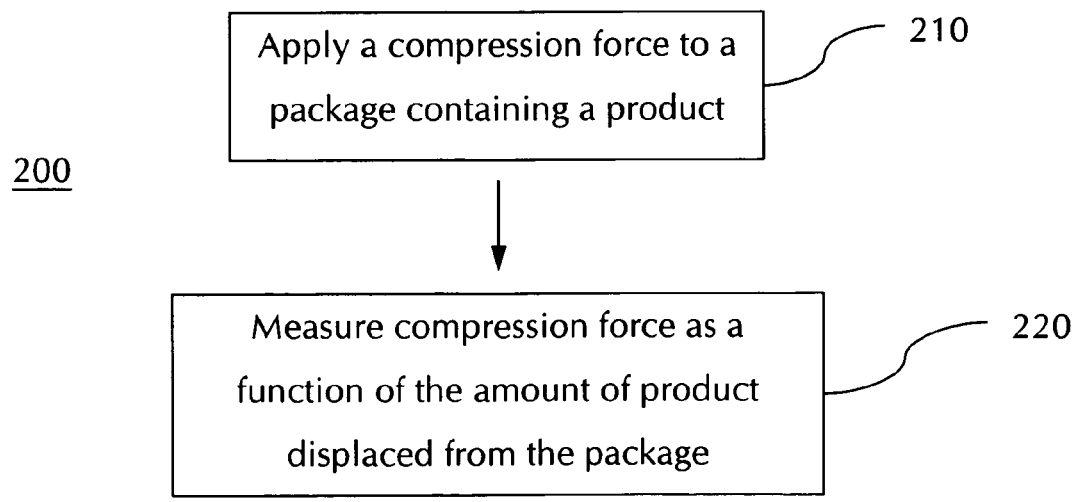
FIG. 2 represents a method of measuring squeeze force of a package containing a fluid.

FIG. 2 represents a method 200 of measuring squeeze force of a package containing a product. The method 200 includes applying a compression force to a package containing a product 210, and measuring the compression force as a function of the amount of product displaced from the package 220. For a package containing a fluid product, the method 200 may provide for measurement of the squeeze force at initiation of fluid flow from the package and may provide for measurement of the squeeze force after at least a portion of the fluid is displaced from the package. In 210 the compression force may be applied to the package manually or automatically.

In 220 the compression force may be measured after at least a portion of the product is displaced from the package. The amount of product may be measured in terms of mass, and the volume change of the package may then be determined based on the mass of product displaced. The amount of product may be measured in terms of volume, and the volume change of the package may then be determined based on the volume of product displaced. If the density of the product in the package is the same as the density of the product outside of the package, then the volume of product displaced will be equal to the volume change of the package. If the density of the product in the package is different from the density of the product outside of the package, then the volume change of the package can be calculated from the volume of product displaced.

If the product in the package is a fluid having a density that does not substantially change when the fluid is displaced from the package, the squeeze force may be expressed as the compression force at a total volume of displaced fluid. The units for squeeze force in this example include lb-f@ x oz., N@ x L, and dynes@ x mL, where "x" is the total volume of fluid displaced at the measured compression force. If the squeeze force is expressed as the compression force at a percentage of displaced fluid volume, the units for squeeze force include lb-f@ y %, N@ y %, and dynes@ y %, where "y" is the volume of fluid displaced as a percentage of the total volume of fluid originally contained in the package. Examples of volume percentages at which compression measurements may be taken include 0% (flow initiation), 10%, 25%, 50%, 75% and 100% of the fluid volume originally contained in the package.

Figure 3:
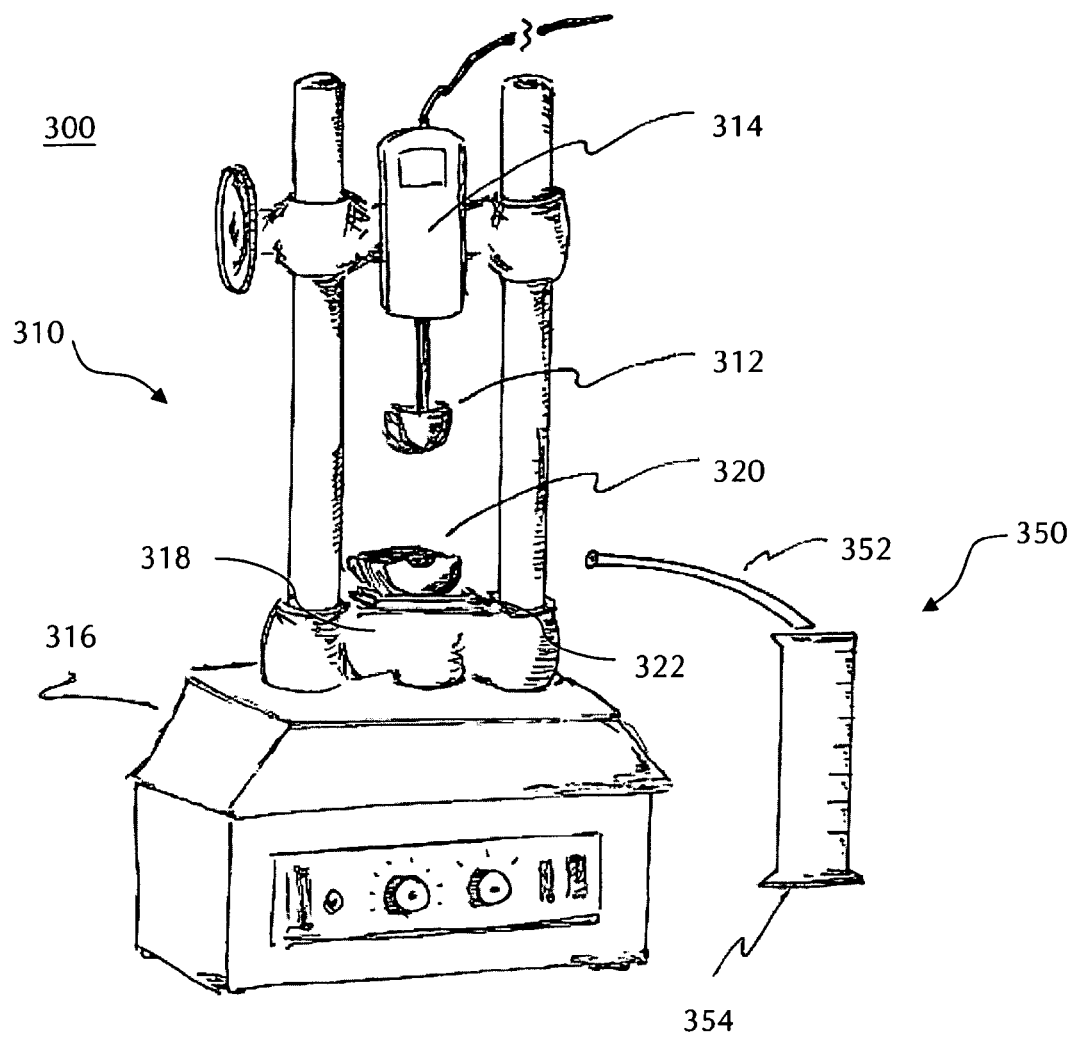
FIG. 3 is a perspective representation of a squeeze force measuring device.

FIG. 3 represents a squeeze force measuring device 300 including a force tester 310 and a fluid gauge 350. The force tester 310 may include a movable crosshead 312 and a force gauge 314 attached to the crosshead. The force tester 310 also may include a test stand 316 having a base 318. The force tester 310 optionally may include a package holder 320 that may secure a package in the device, and the package holder 320 may be secured to the base 318 by an adaptor 322. The fluid gauge 350 may include, for example, a fluid conduit 352 and a receptacle 354.

The squeeze force measuring device 300 may be adaptable for different packages (not shown) having a variety of shapes and sizes, or the device 300 may be configured for packages having a narrow range of shapes and sizes. The device 300 may be configured for one type of package, such as a bottle. An enema bottle is one example of a package that may be evaluated on the basis of squeeze force.

The force gauge 314 provides a measure of the compression force applied to the package. Useful force gauges include those that operate mechanically, electronically, or electro-mechanically. Preferably, the force gauge is provided with a digital readout. When the force gauge 314 is attached to the crosshead 312, the force applied to keep the crosshead moving toward the base 318 of the force tester may be measured.

The test stand 316 may provide a framework for configuring additional components of the force tester 310 relative to the package to be tested. For example, the crosshead 312 may be attached to the test stand 316 above the base 318. The base 318 may include a package holder 320 below the crosshead 312. Examples of test stands include mechanical test stands, pneumatic test stands, motorized test stands, and digital test stands. Specific examples of test stands include those available from Chatillon® (AMTEK TCI Division, Largo, FL.), Cole-Parmer® Instrument Company (Vernon Hills, IL.), and Imada, Inc. (Northbrook, IL.).

The holder 320 may be any rigid object capable of holding the package while allowing a force to be applied to the package. The crosshead 312 may be shaped to fit within the inner dimensions of the holder 320, providing for a substantially complete compression of the package.

The fluid gauge 350 may be any device capable of measuring fluid volume. Examples of fluid gauges include flow meters and fluid receptacles. In one example, the fluid gauge may be a flow meter, such as a flow meter capable of measuring the cumulative flow over a period of time. The flow meter may contain the displaced fluid, or it may direct the fluid to a receptacle or waste system. In another example, the fluid gauge may be a receptacle. The receptacle 354 may be attached to the opening of the package by the fluid conduit 352. Preferably, the receptacle 354 is positioned lower than the package. The receptacle 354 may include markings corresponding to volumetric units, such as the markings of a graduated cylinder. In this configuration, the fluid displaced during the test may be measured visually.

FIG. 4 is a bottom view representation of a crosshead 400 that may apply a compression force to a bottle in a squeeze force measuring device. The crosshead 400 may include a curved lower surface 410, semicircular ends 412 and 414, optional hole 416, and a length 420. FIG. 5 is an end view representation of the crosshead 400 including the curved lower surface 410, the semicircular end 412, and a width 422. FIG. 6 is a side view representation of the crosshead 400 including the semicircular ends 412 and 414, and the optional hole 416. The crosshead 400 may be attached to a test stand through the optional hole 416. For an enema bottle, the length 420 of the crosshead 400 may be from 3 to 7 inches (7.62-17.78 cm), and the width 422 of the crosshead 400 may be from 1 to 3 inches (2.54-7.62 cm).

Figure 7:
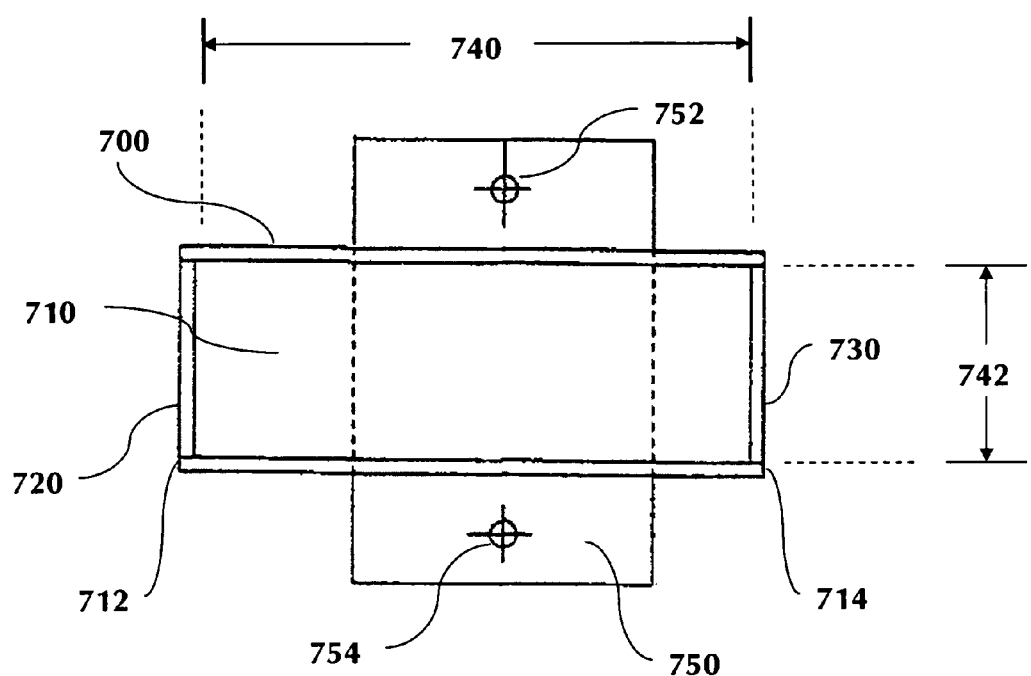
FIG. 7 is a top representation of a holder and adaptor plate.

FIG. 7 is a top view representation of a package holder 700 and an adaptor plate 750. The holder 700 is configured to hold a bottle and includes a curved bottom wall 710 extending linearly from a first end 712 to a second end 714, an end wall 720 attached to the first end 712, and an end wall 730 attached to the second end 714. The holder 700 also has a length 740 and a width 742. The adaptor plate 750 may include holes 752 and 754 for securing the adaptor plate and the holder to a base of a test stand, such as the test stand 316 (FIG. 3).

Figure 8:
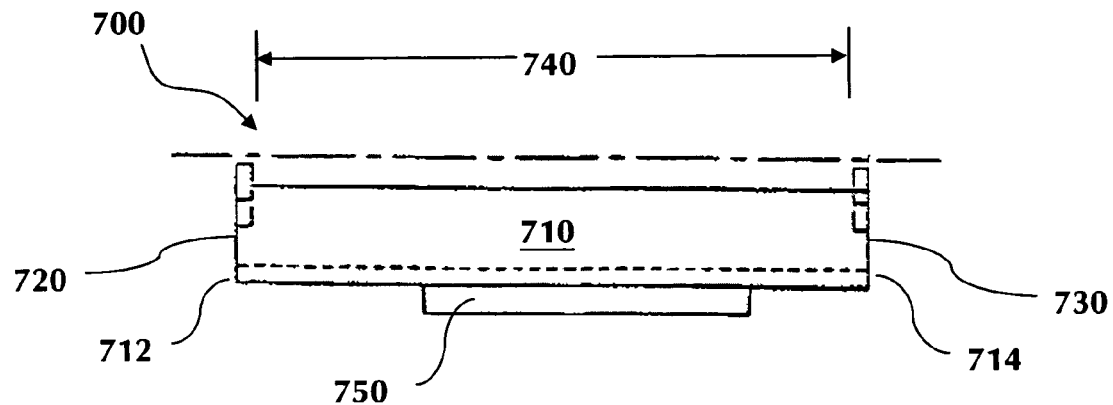
FIG. 8 is a side representation of a holder and adaptor plate.

FIG. 8 is a side view representation of the holder 700 and the adaptor plate 750. The holder 700 includes the curved bottom wall 710 extending linearly along the length 740 from the first end 712 to the second end 714. The end wall 720 is attached to the first end 712, and the end wall 730 is attached to the second end 714.

Figure 9:
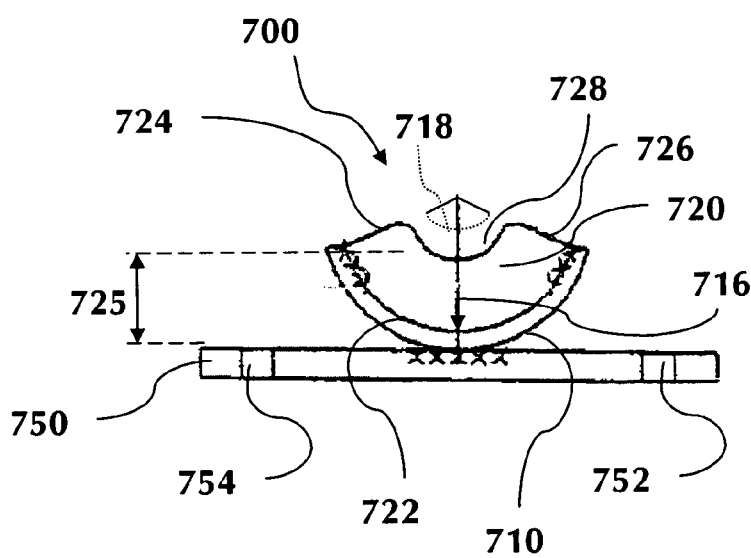
FIG. 9 is an end representation of a holder and adaptor plate.

FIG. 9 is an end view representation of the holder 700 and the adaptor plate 750. The adaptor plate 750 may include the holes 752 and 754 for securing the plate and holder to a base of a test stand. The holder 700 includes the curved bottom wall 710 connected to the end wall 720. The bottom wall 710 has a radius of curvature 716 and an arc 718, which is the angle traversed by the bottom wall.

The end wall 720 has a curved lower edge 722 in contact with the end of the bottom wall 710, two side edges 724 and 726 extending from the bottom wall 710 toward the center of the radius of curvature 716 of the bottom wall, a curved upper edge 728 between the two side edges and concentric with the bottom wall, and a distance 725 between the lower edge 722 and the upper edge 728.

Referring to the holder represented in FIGS. 7-9, the bottom wall 710 is curved, and the arc 718 is large enough to support the bottle during the test, but small enough to allow a compression force to be applied to the bottle. Preferably, the arc 718 of the bottom wall is from 90 degrees to 180 degrees. The end walls 720 and 730 are attached to opposite ends of the bottom wall 710. The end walls 720, 730 may be at right angles to the bottom wall 710, or one or both of the end walls 720, 730 independently may be at an acute or obtuse angle to the bottom wall 710. The curved upper edge 728 may allow access to the opening of a bottle placed in the holder 700 along the longitudinal axis of the bottle.

The length 740, width 742 and radius of curvature 716 of the bottom wall, and the distance 725 between the lower edge 722 and the upper edge 728 of the end wall may be correlated to the dimensions of the bottle or range of bottles to be tested. The shape of the holder also may be coordinated with the shape of the crosshead so the crosshead can fit within the holder. Referring to FIG. 4, the length 420 of the crosshead 400 may be less than or equal to the length 740. Referring to FIG. 5, the width 422 of the crosshead 400 may be less than or equal to the width 742.

In one aspect, the holder is shaped to hold an enema bottle. Commercially available enema bottles typically have a cylindrical body and a nozzle; the body having a length from 4 to 6 inches (10.16-15.24 cm) and a diameter from 1.5 to 2.5 inches (3.81-6.35 cm). For a holder 700 adapted for an enema bottle, the length 740 may be from 3 to 7 inches (7.62-17.78 cm), the width 742 may be from 1 to 3 inches (2.54-7.62 cm), and the radius of curvature 716 may be from 0.75 to 1.5 inches (1.91-3.81 cm). At least one of the end walls of this holder may have the distance 725 from 1 to 2 inches (2.54-5.08 cm).

Figure 10:
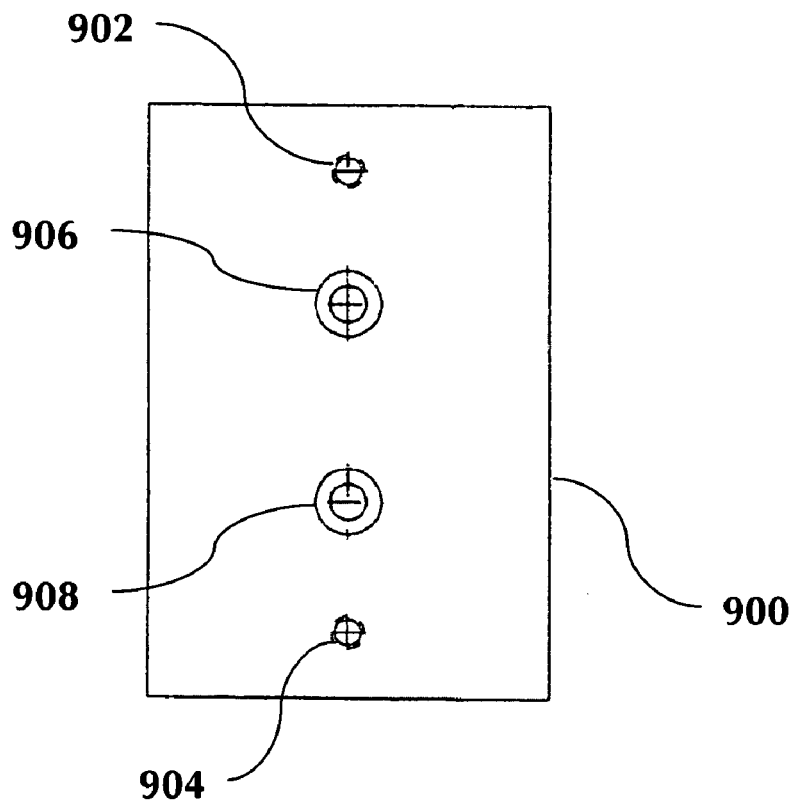
FIG. 10 is a top representation of an adaptor plate.
Figure 11:
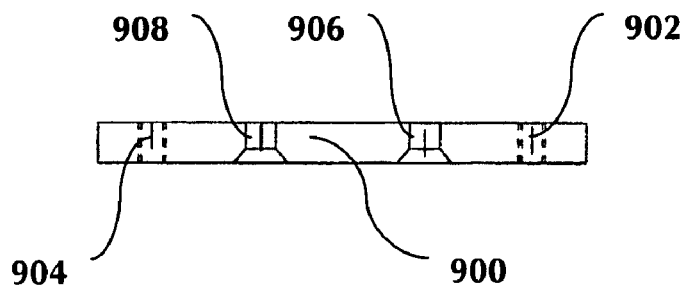
FIG. 11 is a side cross-section representation of an adaptor plate.

FIGS. 10 and 11 are top and side view representations, respectively, of an adaptor plate 900. The adaptor plate 900 may have one or more holes 902, 904, 906 or 908. Mechanical fasteners may be passed through the holes 902 and/or 904 of the adaptor plate 900 to secure the plate to a base of a test stand, such as the base 318 of the test stand 316 (FIG. 3). Examples of mechanical fasteners include screws, bolts and rivets. Mechanical fasteners also may be passed through the holes 906 and/or 908 of the adaptor plate 900 to secure the plate to a holder, such as the holder 700 (FIGS. 7-9). The plate and the holder may be welded together, in addition to or instead of using mechanical fasteners.

Figure 12:
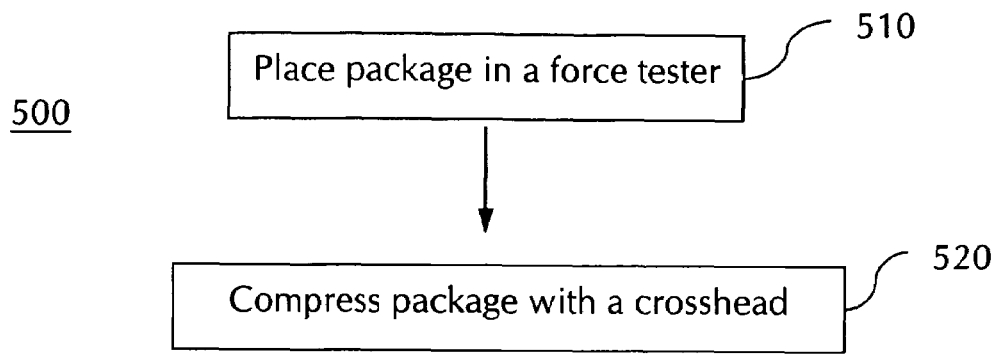
FIG. 12 represents a method of applying a compression force.

FIG. 12 represents a method 500 of applying a compression force to a package. The method 500 includes placing the package in a force tester 510 and compressing the package with a crosshead 520.

Placing the package in a force tester 510 may include positioning the package below the crosshead. The package may be placed directly on the base of a test stand in a position below the crosshead. If a package holder is desired, the package may be inserted in the holder, and the assembled package and holder may be placed on the base of a test stand in a position below the crosshead. In another aspect, the holder may be placed on the base of a test stand in a position below the crosshead, and the package may be inserted in the holder. A package holder may be secured to the base of a test stand, which may include securing the holder to an adaptor plate and securing the adaptor plate to the base of the test stand.

Compressing the package with a crosshead 520 may include moving the crosshead along a path within the force tester such that the volume of the package is reduced. For a package positioned on a base of a test stand and below the crosshead, movement of the crosshead toward the base compresses the package between the crosshead and the base. For a package positioned in a holder, movement of the crosshead toward a bottom wall of the holder compresses the package between the crosshead and the holder. The crosshead may be moved at a constant speed, or it may be moved at a speed that varies over time.

The crosshead may be shaped and positioned so compression is applied at one or more specific regions of the package. For example, the crosshead may be shaped and positioned so compression is applied along a circumference of the package. Circumferential compression may be useful in simulating the squeezing of a package by hand. Circumferential compression also may be facilitated by the shape of a holder for the package. The crosshead also may be shaped and positioned so compression is applied along the length of the package.

Figure 13:
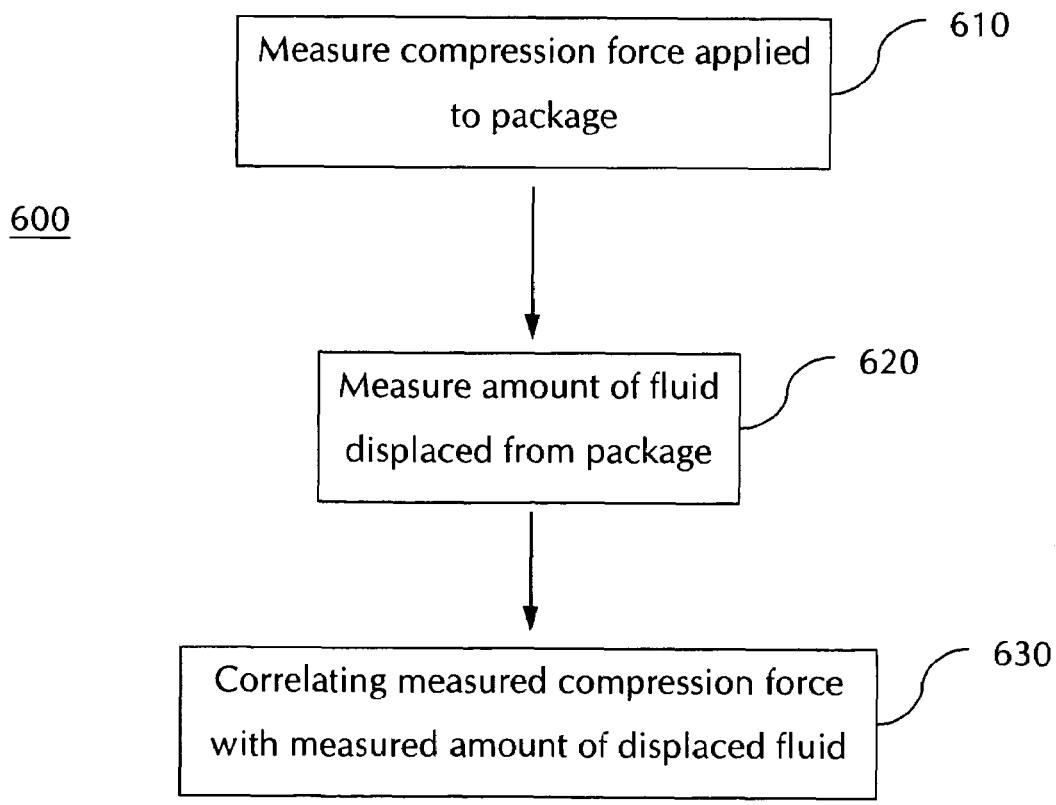
FIG. 13 represents a method of measuring compression force as a function of displaced volume.

FIG. 13 represents a method 600 of measuring compression force as a function of fluid volume displaced from a package, including measuring the compression force applied to the package 610, measuring the amount of fluid displaced from the package 620, and correlating the measured compression force with the measured amount of displaced fluid 630.

In 610, a force gauge may be attached to a crosshead prior to compressing the package with the crosshead. The combined force gauge and crosshead may be pressed against the package manually, and the measurements of the compression force may be taken from the force gauge. The combined force gauge and crosshead may be pressed against the package automatically, such as with a force tester, and the measurements of the compression force may be taken from the force gauge. The compression force measurements may be recorded for evaluation after the package has been compressed.

In 620, the amount of fluid displaced from the package may be measured in different ways, including measuring the mass of the fluid and measuring the volume of the fluid. If the amount of fluid displaced is measured by way of a mass measurement, the fluid may be collected and weighed. If the amount of fluid displaced is measured by way of a volume measurement, a fluid gauge may be connected to the opening of the package prior to compressing the package. In one example, the fluid gauge may be directly attached to the package opening. In another example, the fluid gauge and the package opening may be connected by a fluid conduit. The application of a compression force to a package containing a fluid displaces fluid from the package through the opening and into the fluid gauge, where the displaced fluid volume is measured. The displaced fluid volume measurements may be recorded for evaluation after the package has been compressed.

In 630, the correlation of the measured compression force with the measured amount of displaced fluid provides the squeeze force of the package. If the compression force measurements and the displaced fluid measurements are recorded at particular times during the test, matching the measurements with respect to time may provide the correlation of the compression force with the amount of fluid displaced during the application of that force. The compression force and the amount of displaced also may be measured simultaneously, providing for a direct correlation of the compression force with the amount of displaced fluid.

The following examples are provided to illustrate one or more preferred embodiments of the invention. Numerous variations may be made to the following examples that lie within the scope of the invention.

EXAMPLES

Example 1

Squeeze Force Measuring Device

A Chatillon® UTSM-HS-FS test stand was equipped with a Chatillon® DFM-50 force gauge. The crosshead was an aluminum half-cylinder having a length of 3.25 inches (8.26 cm) and a diameter of 2 inches (5.08 cm). Each semicircular end had a chamfer of 0.125 inch (0.318 cm) by 45 degrees. The crosshead was attached to the test stand through a 10-32 hole in the center of the crosshead. See, for example, FIGS. 4-6.

The test stand was also equipped with a holder for a bottle. The holder was a longitudinal cross-section of a stainless steel cylinder having an original diameter of 2 inches (5.08 cm). The arc of the partial cylinder was 130-degrees. The length of the holder was 5.875 inches (14.92 cm), and each end was connected to a 130-degree section of a stainless steel washer having an outer diameter of 2 inches (5.08 cm) and an inner diameter of $13/16$ inch (2.06 cm). The partial washers were at right angles to the partial cylinder wall. See, for example, FIGS. 7-9.

The holder was affixed to the base of the test stand by a 0.375 inch (0.953 cm) thick stainless steel adaptor plate having a length of 4.5 inches (11.43 cm) and a width of 3 inches (7.62 cm). The holder was centered on the plate and perpendicular with respect to the length of the plate. The plate had two ¼-20 holes, each positioned 0.5 inch (1.27 cm) from an end of the plate and centered 1.5 inches (3.81 cm) from each side of the plate. The plate was affixed to the base of the test stand by screws passing through each of these holes.

Example 2

Squeeze Force Measurements

The squeeze force measuring device of Example 1 was used to acquire the squeeze force date for a variety of enema bottles. The recorded data show that the method used provided a beneficial comparison of squeeze forces for similar packages containing a variety of fluid products. In addition, the recorded data show that the device yielded accurate and consistent squeeze force measurements for similar packages containing a variety of fluid products, and that the holder facilitated the accurate and consistent squeeze force measurements of bottles.

An enema bottle equipped with a nozzle was placed horizontally in the holder, and one end of a flexible tube was attached to the end of the nozzle. The other end of the flexible tube was placed in a graduated cylinder, which was positioned below the holder. The test stand was programmed to lower the crosshead at a rate of 2 inches per minute (5.08 cm/min). The force measurements were recorded at the initiation of flow and at particular displaced volumes as measured in the graduated cylinder.

A FLEET® saline enema for adult use contained 133 milliliters (mL) of total fluid, of which 118 mL typically may be displaced by a user. The force measurements were recorded at the initiation of flow and at displaced volumes of 15 mL, 30 mL, 45 mL, 60 mL and 75 mL as measured in the graduated cylinder. The squeeze force measurement was repeated for a total of 20 samples.

A FLEET® bisacodyl enema contained 37 mL of total fluid, of which 30 mL typically may be displaced by a user. The force measurements were recorded at the initiation of flow and at displaced volumes of 5 mL, 10 mL, 15 mL and 20 mL. The squeeze force measurement was repeated for a total of 3 samples.

A FLEET® mineral oil enema contained 133 mL of total fluid, of which 118 mL typically may be displaced by a user. The force measurements were recorded at the initiation of flow and at displaced volumes of 15 mL, 30 mL, 45 mL, 60 mL and 75 mL. The squeeze force measurement was repeated for a total of 3 samples.

A FLEET® pediatric saline enema contained 66 mL of total fluid, of which 59 mL typically may be displaced by a user. The force measurements were recorded at the initiation of flow and at displaced volumes of 10 mL, 20 mL, 30 mL and 40 mL. The squeeze force measurement was repeated for a total of 3 samples.

Figure 14:
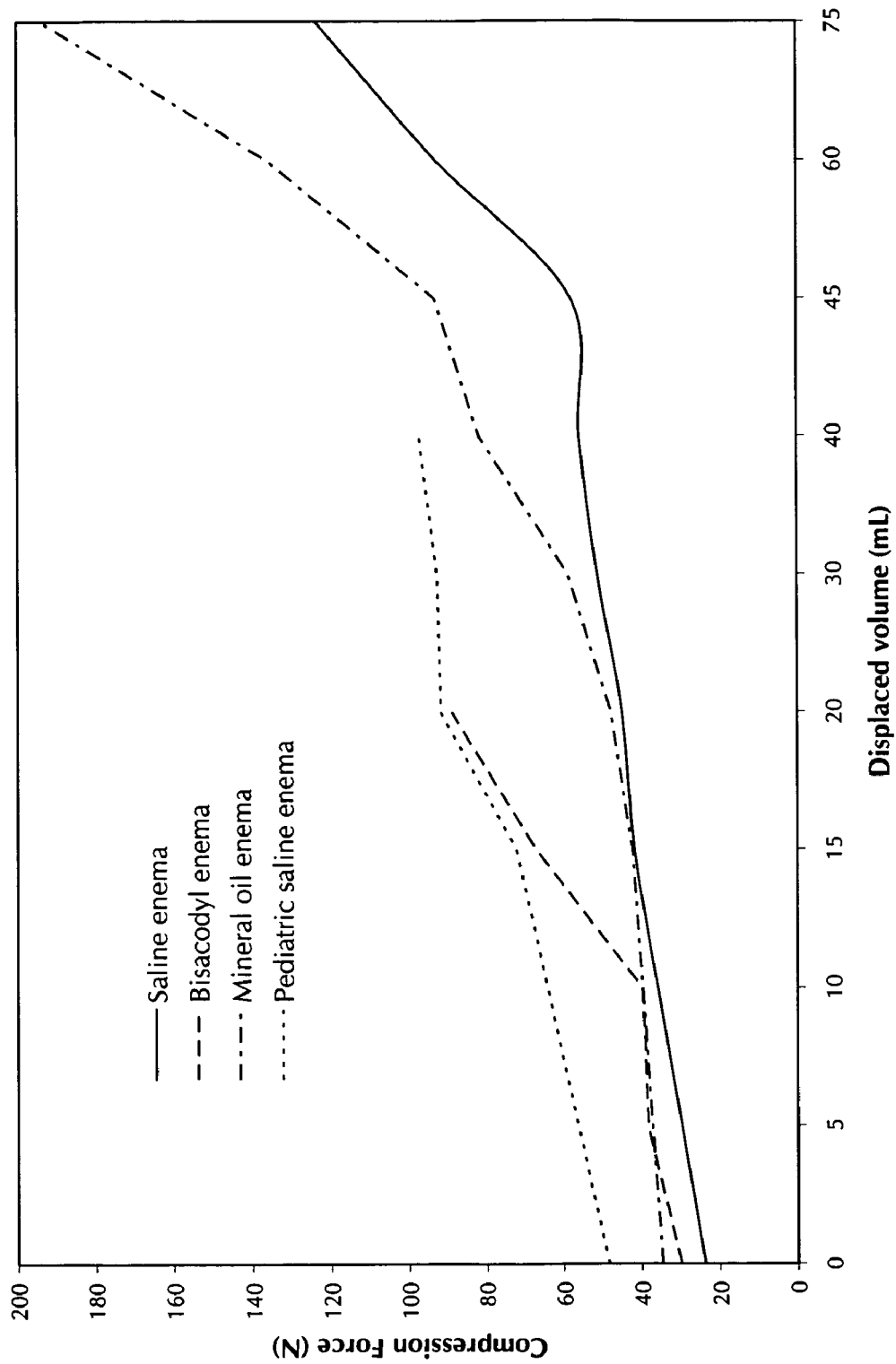
FIG. 14 is a graph of squeeze force measurements.

FIG. 14 is a graph of the compression force as a function of total displaced fluid volume. The plots represent the average values for each type of enema. The squeeze force measurements were taken from the correlations represented in this graph.

TABLE 1

Squeeze forces of enema bottles

| | Squeeze force measurements | | | | | | | | | |
|---|---|---|---|---|---|---|---|---|---|---|
| Fluid | N @ Initiation | N @ 5 mL | N @ 10 mL | N @ 15 mL | N @ 20 mL | N @ 30 mL | N @ 40 mL | N @ 45 mL | N @ 60 mL | N @ 75 mL |
| Saline | 23.71 | — | — | 41.77 | — | 51.24 | — | 58.09 | 92.92 | 123.7 |
| Bisacodyl | 29.89 | 38.34 | 39.68 | 67.17 | 88.83 | — | — | — | — | — |
| Mineral oil | 34.61 | — | — | 42.26 | — | 58.85 | — | 93.19 | 136.2 | 193.72 |
| Pediatric saline | 48.35 | — | 64.23 | — | 91.72 | 92.61 | 97.28 | — | — | — |

The values in Table 1 also can be expressed in terms of the percentage of the fluid volume originally present in the bottle. For the saline enema for adult use, these values correspond to 41.77 N@11.3%; 51.24 N@22.6%; 58.09 N@33.8%; 92.92 N@45.1%; and 123.7 N@56.4%, respectively. For the bisacodyl enema, these values correspond to 38.34 N@13.5%; 39.68 N@27.0%; 67.17 N@40.5%; and 88.83 N@54.1%, respectively. For the mineral oil enema, these values correspond to 42.26 N@11.3%; 58.85 N@22.6%; 93.19 N@33.8%; 136.2 N@45.1%; and 193.72 N@56.4%, respectively. For the pediatric saline enema, these values correspond to 64.23 N@15.2%; 91.72 N@30.3%; 92.61 N@45.5%; and 97.28 N@60.6%, respectively.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of measuring squeeze force, comprising:
   applying a compression force to a package;
   measuring more than once the compression force applied to the package;
   measuring more than once the volume change of the package; and
   correlating the measured compression force with the measured volume change.

2. The method of claim 1, where the applying comprises:
   placing the package in a force tester comprising a crosshead; and
   compressing the package with the crosshead.

3. The method of claim 2, where the placing comprises positioning the package below the crosshead.

4. The method of claim 3, where the force tester further comprises a holder; and
   the placing comprises inserting the package in the holder.

5. The method of claim 4, where the compressing comprises moving the crosshead toward a bottom of the holder.

6. The method of claim 2, where the force tester further comprises a test stand comprising a base; and
   the placing comprises placing the package on the base.

7. The method of claim 6, where the compressing comprises moving the crosshead toward the base.

8. The method of claim 1, where the package comprises a fluid.

9. The method of claim 8, where the measuring is performed at initiation of fluid flow.

10. The method of claim 8, where the measuring is performed after at least a portion of the fluid is displaced from the package.

11. The method of claim 10, where the measuring comprises calculating a percentage of the fluid that is displaced from the package.

12. The method of claim 8, where the measuring comprises:
    measuring the compression force applied to the package;
    measuring the amount of fluid displaced from the package; and
    correlating the measured compression force with the measured amount of displaced fluid.

13. A method of measuring squeeze force of a package, comprising:
    placing the package in a force tester below a movable crosshead;
    compressing the package with the crosshead by a compression force;
    measuring more than once the compression force applied to the package with a force gauge attached to the crosshead;
    measuring more than once the volume change of the package; and
    correlating the measured compression force with the measured volume change.

14. The method of claim 13, where the package comprises a product.

15. The method of claim 14, where the measuring the volume change comprises measuring the amount of product displaced from the package.

16. The method of claim 15, where the product is a fluid.

17. The method of claim 16, where the fluid is selected from the group consisting of liquids, gels, creams, pastes and thixotropic materials.

18. The method of claim 16, where the measuring the amount of product displaced comprises measuring the mass of fluid displaced from the package.

19. The method of claim 16, where the measuring the amount of product displaced comprises measuring the volume of fluid displaced from the package.

20. The method of claim 19, further comprising connecting the package to a fluid gauge prior to the compressing.

21. The method of claim 13, where the force tester comprises a test stand comprising a base;
    the placing comprises placing the package on the base; and
    the compressing comprises moving the crosshead toward the base.

22. The method of claim 13, where:
    the placing comprises inserting the package in a holder; and
    the compressing comprises moving the crosshead toward a bottom of the holder.

23. The method of claim 22, where the force tester comprises a test stand comprising a base, and the placing further comprises securing the holder to the base.

24. The method of claim 22, where the crosshead is shaped to fit the inner dimensions of the holder.

25. The method of claim 22, where the package is a bottle.

26. The method of claim 25, where the package is compressed along the circumference of the package.

27. The method of claim 22, where the package is compressed along the length of the package.

* * * * *